United States Patent [19]

Task

[11] Patent Number: 4,764,007
[45] Date of Patent: Aug. 16, 1988

[54] GLARE SUSCEPTIBILITY TESTER

[75] Inventor: Harry L. Task, Dayton, Ohio

[73] Assignee: The United States of America as represented by the Secretary of the Air Force, Washington, D.C.

[21] Appl. No.: 831,909

[22] Filed: Feb. 24, 1986

[51] Int. Cl.$^4$ .............................................. A61B 3/02
[52] U.S. Cl. .................................. 351/243; 351/222; 351/246
[58] Field of Search ............... 351/211, 221, 243, 222, 351/246

[56] References Cited

U.S. PATENT DOCUMENTS

| | | |
|---|---|---|
| 2,321,915 | 6/1943 | Higley . |
| 2,536,305 | 1/1951 | Morton . |
| 3,011,394 | 12/1961 | Sherman et al. . |
| 3,469,904 | 9/1969 | Allen . |
| 3,533,683 | 10/1970 | Stark et al. . |
| 3,684,355 | 8/1972 | Molner . |
| 4,533,222 | 8/1985 | Ishikawa . |

Primary Examiner—Rodney B. Bovernick
Attorney, Agent, or Firm—Bobby D. Scearce; Donald J. Singer

[57] ABSTRACT

An optical instrument and method for measuring susceptibility to glare of a human vision system is described which comprises a glare light source of preselected intensity sufficient to generate glare in the vision system of a subject, an acuity target having first opaque or partially transparent areas and second translucent areas defining a pattern of recognizable indicia on the target, a housing supporting target and source side-by-side for simultaneous viewing by the subject, and a reflective surface within the housing for directing light from the source onto the back surface of the target for substantially uniform transillumination of the target with light from the source. Optional optical filters may be placed between the source and subject, target and subject, or source and reflective surface, for selectively filtering light viewed by the subject. A movable cover plate may be included for selectively exposing the source to the subject in certain glare susceptibility measurements.

18 Claims, 3 Drawing Sheets

GLARE SUSCEPTIBILITY TESTER

RIGHTS OF THE GOVERNMENT

The invention described herein may be manufactured and used by or for the Government of the United States of all governmental purposes without the payment of any royalty.

BACKGROUND OF THE INVENTION

The present invention relates generally to testing equipment and methods for measuring visual functions of the human vision system, and more particularly to an instrument and method for measuring visual capability under dim light, glare conditions.

The ability of a person to detect objects in the visual field is in part dependent upon the sensitivity to glare of that person's vision system. The degree of glare susceptibility of the human vision system is the overall effect of several contributing factors including the presence of light scattering particulate matter in the vitreous humor of the eye, congenital or injury induced cloudiness in the cornea or lens, the presence of cataracts, other changes in transparency of intraocular media due to the aging process, and similar and related factors.

The invention provides an instrument and method for measuring the susceptibility to glare of a human subject in a non-invasive manner. The instrument comprises a glare light source that also serves to illuminate a translucent acuity target. The housing for the light source and target includes a light baffle whereby light from the glare source is directed forwardly toward the subject and rearwardly through an optional optical filter for reflection off a mirror or diffusely reflective surface for transillumination of the acuity target disposed beside the glare source. The glare source is therefore observed by the subject simultaneously with the viewing of the acuity pattern. The observed glare obscures a portion of the pattern of the acuity target to a degree corresponding to the susceptibility to glare of the vision system of the subject. A single light source for both a glare source and acuity chart transillumination accords fixed calibration to the instrument. The instrument may be battery powered for portability.

The invention therefore provides a unique optical instrument and method for directly measuring visual acuity under substantially point source glare conditions, and, accordingly, may be highly useful in the assessment of certain physiological conditions of the normally transparent media of the eye. Further, the invention may be used for such purposes as monitoring post-surgical conditions of the eye, monitoring ocular trauma conditions or surgical or ophthalmic procedures, measuring severity of cataracts, defining analytical bases for glare susceptibility in individuals, and determining effects of contact lenses or other refractive elements on corneal physiology. The method of the invention is an ideal screening procedure for persons in night vision performance sensitive jobs such as night flying, refueling, driving, etc.

It is, therefore, a principal object of the invention to provide an instrument and method for measuring visual capability of the human vision system under dim light, glare conditions.

It is a further object of the invention to provide an instrument and method for measuring visual acuity of the human vision system under point source glare conditions.

It is yet another object of the invention to provide an improved chart for measuring visual acuity of the human vision system.

These and other objects of the invention will become apparent as the detailed description of certain representative embodiments thereof proceeds.

SUMMARY OF THE INVENTION

In accordance with the foregoing principles and objects of the invention, a novel optical instrument and method for measuring glare susceptibility in a human vision system is described which comprises a glare light source of preselected intensity sufficient to generate glare in the vision system of a subject, an acuity target having first opaque or partially transparent areas and second translucent areas defining a pattern of recognizable indicia on the target, a housing supporting target and source side-by-side for simultaneous viewing by the subject, and a reflective surface within the housing for directing light from the source onto the back surface of the target for substantially uniform transillumination of the target with light from the source. Optional optical filters may be placed between the source and subject, target and subject, or source and reflective surface, for selectively filtering light viewed by the subject. A movable cover plate may be included for selectively exposing the source to the subject in certain glare susceptibility measurements.

DESCRIPTION OF THE DRAWINGS

The invention will be more clearly understood from the following detailed description of representative embodiments thereof read in conjunction with the accompanying drawings wherein.

DETAILED DESCRIPTION

Figure 1:
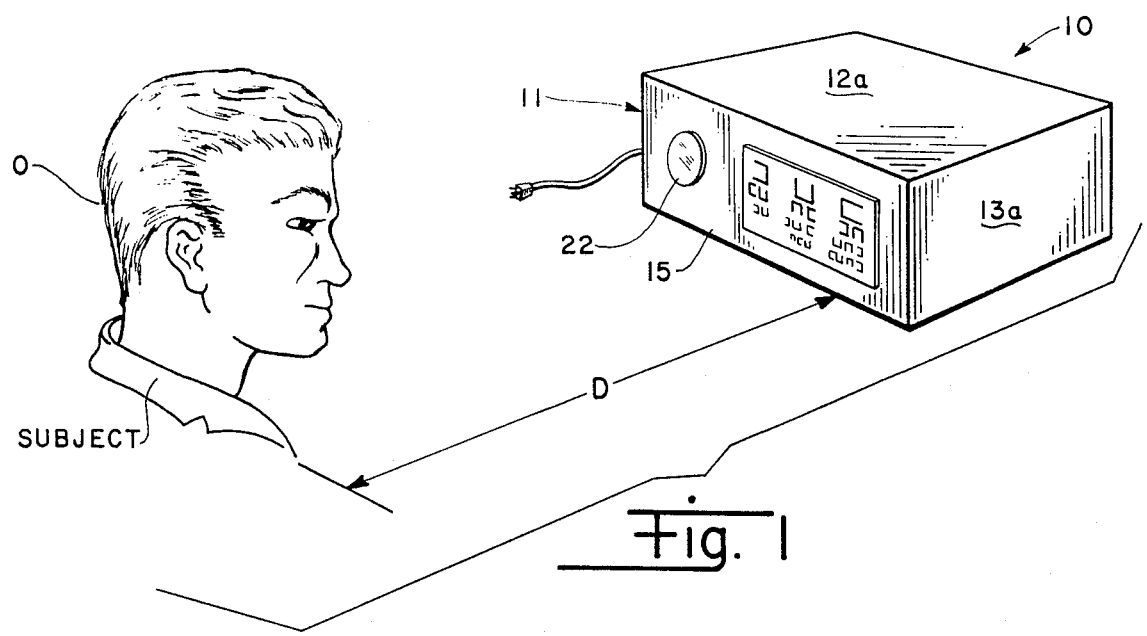
FIG. 1 is a perspective view of a representative glare susceptibility tester of the invention as viewed by a subject.
Figure 2:
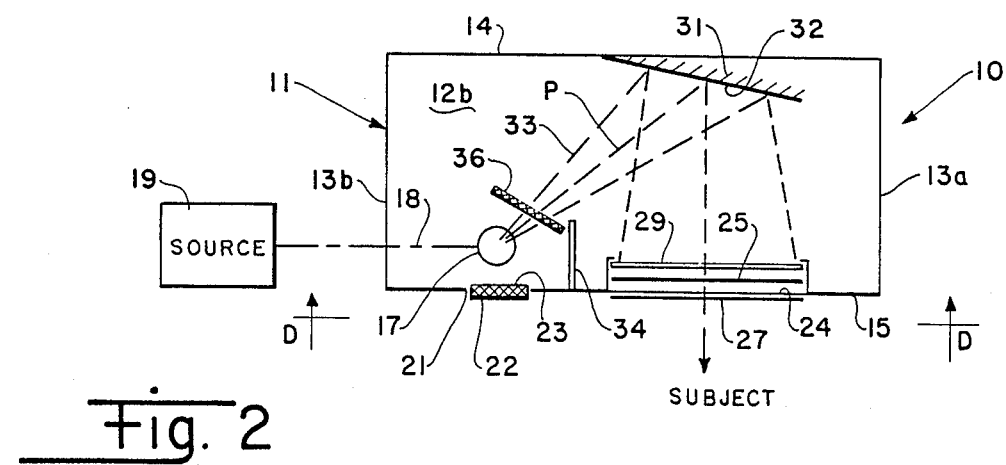
FIG. 2 is a schematic plan view of the optical components of the representative tester illustrated in FIG. 1.

Referring now to the drawings, FIG. 1 shows a perspective view of a representative glare susceptibility tester 10 of the invention positioned for viewing by subject O. FIG. 2 is a schematic plan view of the interior component parts of tester 10. In the representative embodiment depicted in FIG. 2, tester 10 comprises a substantially closed housing 11 including top and bottom walls 12a,b, side walls 13a,b, back panel 14, and front panel 15. For convenience of construction and use of tester 10 as hereafter detailed, front panel 15 and rear panel 14 may be removably attached to the remainder of housing 11 by screws or the like (not shown), although such structural details are not considered limiting of the invention.

The optical components of the invention may include those suggested in the plan view of FIG. 2. A glare source 17 comprising an incandescent light source, light emitting diode, fluorescent source, laser, or the like, is connected via electrical means 18 to a source of power 19, such as an AC outlet, battery, etc. Source 17 is disposed near a first optical opening 21 in front panel 15 for viewing by subject O as suggested in FIG. 1. A hinged or slidable coverplate 22 may be included to selectively expose source 17. In certain applications of tester 10, such as to measure glare susceptibility at reduced levels of glare source intensity, it may be desirable to include an optical filter 23 over glare source 17, and accordingly, panel 15 may include a support for filter 23 at opening 21.

A second optical opening 24 is defined in panel 15, as suggested in FIG. 2, and is of appropriate size and shape to support a patterned visual acuity target or chart 25 such as described in detail below in relation to FIGS. 4–8b. Panel 15 may further include means to support a tinted filter plate 27 over target 25 for certain tests (such as glare susceptibility, acuity, or contrast threshold). A diffuser palte 29 may also be included at opening 23 behind target 25.

Mirror 31 supporting a reflective surface 32 is mounted in any convenient fashion within housing 11, near rear panel 14, to define an optical path P along which light 33 from source 17 may be reflected onto diffuser plate 29 for illumination of target 25. In order that stray light from source 17 does not directly illuminate diffuser plate 29 and target 25, a light baffle 34 in the form of a short wall segment of housing 11 may be included in position substantially as shown in FIG. 2. The surface of baffle 34 and other interior surfaces of housing 11 may be coated with light absorbing material or may be painted, as desired, to minimize extraneous light reflection within housing 11. An optional optical filter 36 may be mounted at any convenient location along optical path P between source 17 and target 25, such as shown, for use in glare susceptibility tests wherein various preselected ratios of target luminance to glare source intensity are utilized.

Figure 3:
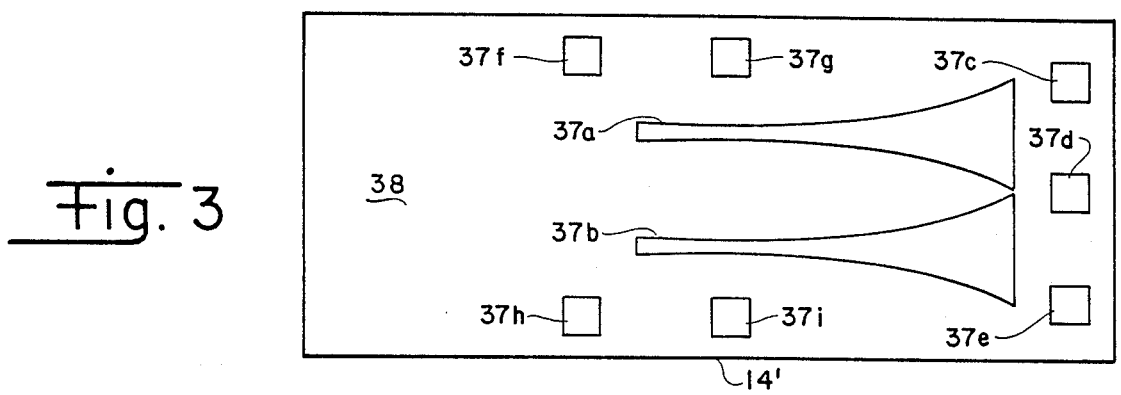
FIG. 3 is an alternative structure of the tester of FIG. 2 for providing uniform low-level luminance to the target.

In certain low intensity, low contrast and low illumination tests utilizing tester 10 it may be critical to obtain uniform, low level transillumination of target 25. Accordingly, in an alternative embodiment of tester 10, a rear panel 14' of housing 11 may be configured as suggested in FIG. 3. Panel 14' comprises a diffusely reflective surface defining diffuse light reflective areas 37a–i painted white on an interior surface 38 comprising a coating of optical flocking material. The geometric pattern of reflective areas 37a–i are developed empirically and depend upon the geometrical arrangement and physical size of housing 11 and the optical components comprising tester 10.

Figure 4:
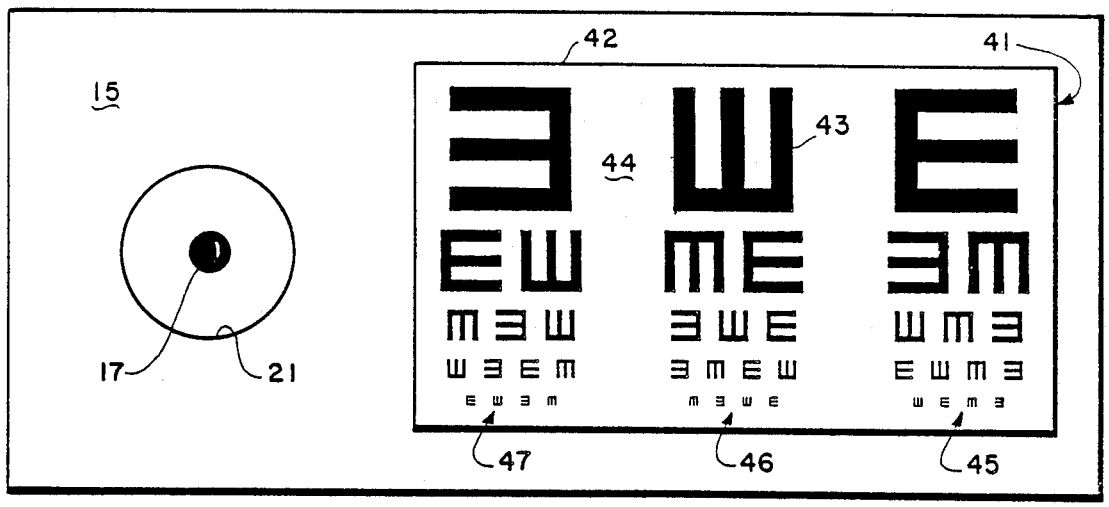
FIGS. 4, 5, 6, 7a and 8a illustrate representative acuity targets usable with the invention.

Referring now to FIGS. 4–8b, shown therein are representative charts comprising acuity targets useful in visual acuity determinations according to the method of the invention. Each acuity target may comprise a plurality of translucent recognizable indicia of predetermined sizes and groupings defined on a substantially opaque background. Alternatively, the acuity target may comprise opaque or semi-opaque indicia defined on a translucent background. For example, in the view of FIG. 4, which may be taken as a view along lines D—D of FIG. 2, acuity target 41 comprises a plate 42 defining a plurality of translucent indicia 43 on an otherwise substantially opaque background 44. Indicia 43 may be arranged in any predetermined number of groups, such as designated 45,46,47, each of which may include indicia of various sizes and orientations. Target 41 of FIG. 4 illustrates the use of the well-known "tumbling E" design, although other configurations such as the Snellen prong design suggested in FIG. 1 may be equally desirable for use. Each patterned grouping 45,46,47 of indicia are placed on chart 41 locations corresponding to respective predetermined spacings from glare source 17 when chart 41 is installed within opening 24 of panel 15. The glare effect of source 17 diminishes for target groupings progressively further from glare source 17, and accordingly, laterally placed groups 45,46,47 provide a measure of the glare effect of source 17. This measure may be correlated with the degree of haze in a transparency.

Figure 6:
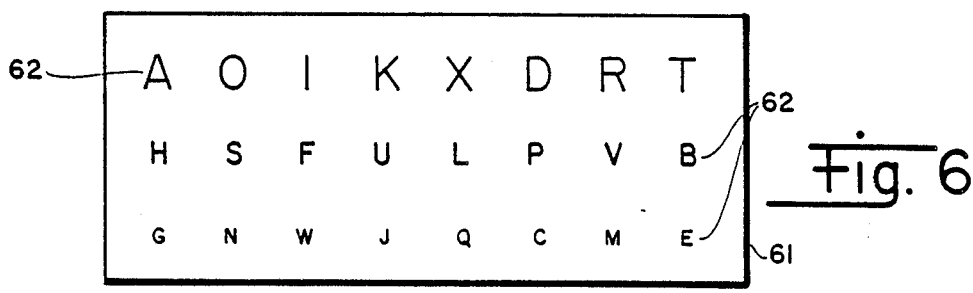
Figure 5:
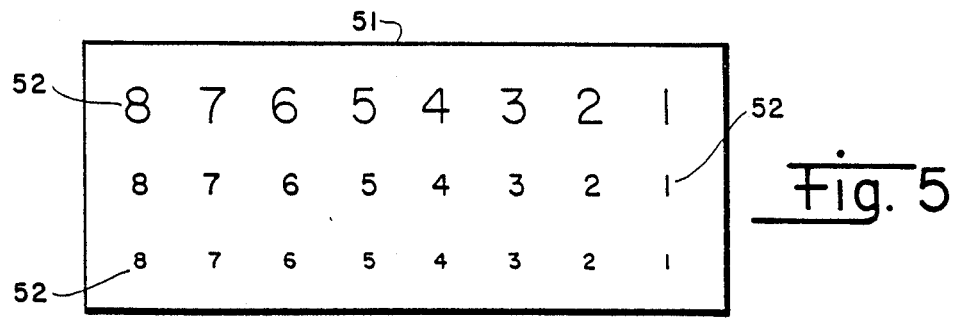

In alternative embodiments of acuity target 25 (FIG. 2), target 51 of FIG. 5 may comprise a number chart displaying translucent (or opaque) indicia 52 of various sizes on a substantially opaque (or translucent) background, and wherein successively higher (or lower) numbers correspond to greater distances from the glare source; chart 61 of FIG. 6 shows spaced random letters 62 of various sizes corresponding to predetermined angular extents from a glare source. It is understood that other patterned charts and indicia may be used as would occur to one with skill in the field of the invention guided by these teachings, the specific arrangements shown not being exhaustive of those reasonably within the scope of these teachings.

Figures 7A, 7B:
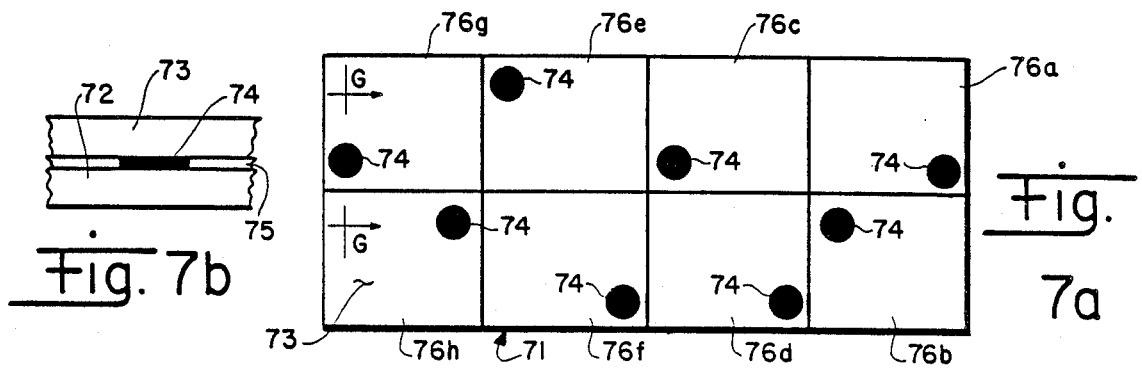
FIG. 7b is a sectional view of the target of FIG. 7a taken along lines G—G.

Of particular use in glare susceptibility measurements according to the invention is the novel chart 71 structure illustrated in FIGS. 7a and 7b, FIG. 7b being an enlarged sectional view of the chart of FIG. 7a taken along lines G—G. Chart 71 comprises a pair of translucent sheets 72,73 with a plurality of thin shaped disks of preselected transmissivities (i.e., opaque or partially transparent) sandwiched therebetween. As illustrated in FIG. 7b, the shaped disks may be embodied in the form of a plurality of dark shapes 74 on a transparent or translucent background of a photographic film 75. Sheets 72,73 may comprise any suitable material for the application described; in a unit built in demonstration of chart 71, plastic sheets were found preferable. Shapes 74 are illustrated as circular, although ovals, rings, rectangles, stars, tumbling E's or any other recognizable geometric shapes in any desired sizes may also be used. A grid pattern of any suitable plurality of grid sections, such as illustrated as 76a–h, are defined on chart 71. A shape 74 is included in each grid section randomly placed at one of the upper or lower, left or right positions in each section as suggested in FIG. 7a. The effect of light passing through sheets 72,73 past each shape 74 presents fuzzy test pattern shapes of various contrasts, the degree of definition of the edges of shapes 74 varying approximately inversely with shape 74 size and overall chart 71 thickness.

Figure 8A:
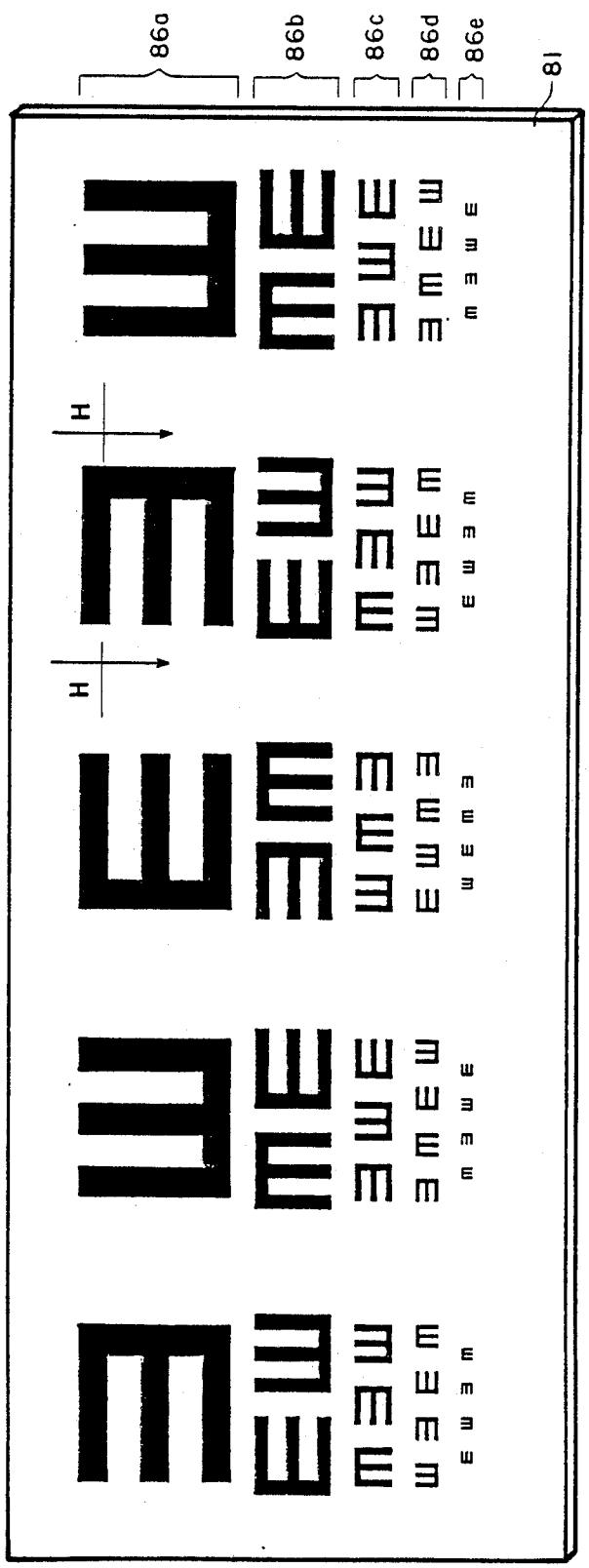
Figure 8B:
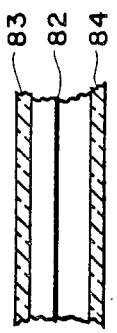
FIG. 8b is a sectional view of the target of FIG. 8a taken along lines H—H.

FIGS. 8a and 8b illustrate another novel chart structure of particular utility in glare susceptibility measurements using tester 10 of the invention. FIG. 8b is a view of the chart of FIG. 8a taken along lines H—H. Chart 81 of FIG. 8a comprises a plurality of recognizable translucent indicia on a substantially opaque background. For illustrative purposes, the tumbling E design is shown on chart 81 although other indicia may be used. As shown in FIG. 8b, chart 81 may preferably comprise a film 82 containing the indicia sandwiched between a clear plastic layer 83 and a translucent layer 84. The indicia are arranged in a selected plurality of groups such as shown as 85a–e, the groups having progressively lower transmissivities nearer the right side of the chart (i.e., nearer a glare source), which provides progressively lower contrasts nearer the glare source. Additionally, vertical groupings 86a–e may be configured to correspond respectively to various overall vision capabilities (e.g., 20/200, 20/100, 20/80, 20/60, and 20/40).

In the use of tester 10 of the invention, and with reference again to FIGS. 1 and 2, subject O is positioned a predetermined distance D from tester 10 so that a view such as that illustrated in FIG. 4 is seen by subject O. Glare source 17 is in the field of view of subject O and causes light to be scattered within the eye of subject O onto those portions of the retina upon which the acuity target pattern is imaged. The glare reduces the contrast of a portion of the acuity pattern and reduces its readability to subject O for acuity target groupings near glare source 17, the target being obscured in an amount corresponding to the degree of glare susceptibility of subject O for the given conditions of glare source intensity, contrast, background illumination, and observation distance D. The visual acuity of subject O is determined for each of the targets with and without coverplate 22 over glare source 17, the difference in acuity with and without glare source 17 being the visual capability loss of subject O due to glare.

Each eye of subject O may be measured separately for glare susceptibility using suitable eye shields, or both eyes may be measured simultaneously, as desired. Further, glare source intensity, optical filter components, and observation distance may be varied as appropriate in any test or series of tests contemplated herein. The corresponding test results may be compared to a set of standards to determine the degree of glare susceptibility of a subject, and to compare the results to an average or norm for a class to which the subject belongs.

The invention therefore provides a novel optical instrument and method for testing glare susceptibility in a human vision system. It is understood that certian modifications to the invention as described may be made, as might occur to one with skill in the field of the invention, within the scope of the appended claims. Therefore, all embodiments contemplated hereunder which achieve the objects of the invention have not been shown in complete detail. Other embodiments may be developed without departing from the spirit of the invention or from the scope of the appended claims.

I claim:

1. An optical instrument for measuring glare susceptibility of a subject, comprising:
   (a) a glare source of light of preselected intensity;
   (b) an acuity target having a front surface and a back surface and defining first areas substantially opaque to light from said source and second areas translucent to light from said source, said first areas and said second areas defining a pattern of a plurality of recognizable indicia of various preselected sizes and preselected respective spacings for each of said various preselected sizes on said target;
   (c) means for supporting said target adjacent said source with each of said plurality of recognizable indicia disposed a preselected radial distance from said source, corresponding to the respective spacing of said each of said plurality of recognizable indicia on said target, for simultaneous viewing of said source and said plurality of recognizable indicia by said subject; and
   (d) optical means for directing light along an optical axis from said source onto said back surface of said target and for substantially uniformly transilluminating said target.

2. The instrument as recited in claim 1 further comprising an optical filter covering said source.

3. The instrument as recited in claim 1 further comprising an optical filter along said optical axis between said source and said target.

4. The instrument as recited in claim 1 further comprising a light diffusing plate adjacent said target at said back surface.

5. The instrument as recited in claim 1 wherein said means for supporting said target and said source comprises a substantially closed housing.

6. The instrument as recited in claim 5 wherein said optical means includes a mirror mounted within said housing behind said target and said source and along said optical axis for reflecting light from said source onto said back surface of said target.

7. The instrument as recited in claim 5 wherein said housing includes an innner surface thereof behind said source and said target, said inner surface including diffusely reflective areas on a light absorbing background, said diffusely reflective areas being preselected in size and configuration to diffusely reflect light from said source along said optical axis and thereby substantially uniformly illuminate said back surface of said target.

8. The instrument as recited in claim 1 further comprising a movable cover plate for said source for selectively exposing said source to said subject.

9. An optical instrument for measuring glare susceptibility of a subject, comprising:
   (a) a substantially closed housing, said housing including a first side and a second side, said first side defining therein first and second optical openings spaced apart a preselected distance;
   (b) a glare source of light of preselected intensity disposed within said housing near said first opening for viewing by said subject;
   (c) an acuity target having a front surface and a back surface and being mounted on said housing at said second opening, said target defining first areas substantially opaque to light from said source and second areas translucent to light from said source, said first areas and said second areas defining a pattern of a plurality of recognizable indicia of various preselected sizes and preselected respective spacings for each of said various preselected sizes on said target, whereby each of said plurality of recognizable indicia is disposed a preselected radial distance from said source for simultaneous viewing of said source and said plurality of recognizable indicia by said subject; and
   (d) optical means within said housing for direciton light along an optical axis from said source onto said back surface of said target and substantially uniformly transilluminating said target by light from said source.

10. The instrument as recited in claim 9 further comprising an optical filter covering said source.

11. The instrument as recited in claim 9 further comprising an optical filter disposed along said optical axis between said source and said back surface of said target.

12. The instrument as recited in claim 9 further comprising a light diffusing plate adjacent said target at said back surface.

13. The instrument as recited in claim 9 wherein said optical means includes a mirror mounted along said optical axis within said housing near said second side thereof and behind said target and said source.

14. The instrument as recited in claim 9 wherein said optical means includes on an inner surface of said second side of said housing diffusely reflective areas on a light absorbing background, said diffusely reflective areas being preselected in size and configuration to diffusely reflect light from said source and thereby substantially uniformly transilluminate said target.

15. The instrument as recited in claim 9 further comprising a movable cover plate mounted to said housing at said first opening for selectively exposing said source to said subject.

16. An optical chart comprising:
 (a) first and second translucent sheets; and
 (b) a plurality of thin disks of respective preselected shapes and light transmissivities sandwiched between said first and second translucent sheets and disposed in preselected spaced relationship to each other.

17. The chart as recited in claim 16 wherein said plurality of disks comprise spaced apart and well defined exposed portions of photographic film on a substantially transparent background of said film and wherein said film is sandwiched between said first and second translucent sheets.

18. A method for measuring glare susceptibility of a subject comprising the steps of:
 (a) providing a glare source of light of preselected intensity;
 (b) providing an acuity target in side-by-side relationship to said source for simultaneous viewing of said source and said target by said subject, said target having a front surface and a back surface and defining first areas substantially opaque to light from said source and second areas translucent to light from said source, said first area and said second area defining a pattern of a plurality of recognizable indicia of various preselected sizes and preselected respective spacings for each of said various preselected sizes on said target, whereby each of said plurality of recognizable indicia is disposed a preselected radial distance from said source for simultaneous viewing of said source and said plurality of recognizable indicia by said subject;
 (c) substantially uniformly transilluminating said target by directing light along an optical axis from said source onto said back surface of said target;
 (d) selectively exposing said source to said subject, whereby the subject's view of said target is obscured to an obervable degree by glare from said source; and
 (e) determining the degree to which the subject's view of said target is obscured by glare of said source.

* * * * *

UNITED STATES PATENT AND TRADEMARK OFFICE
CERTIFICATE OF CORRECTION

PATENT NO. : 4,764,007

DATED : August 16, 1988

INVENTOR(S) : Harry L. Task

It is certified that error appears in the above-identified patent and that said Letters Patent is hereby corrected as shown below:

Title page, item [73], the word "The" should be deleted.

Column 3, line 21, "palte" should be ---plate---.
Column 4, line 6, after "41" should appear ---at---.
Column 5, line 40, "certian" should be ---certain---.
Column 6, line 21, in claim 7, second line, "innner" should be ---inner---.
Column 6, line 56, in claim 9, subparagraph (d), "direciton" should be ---directing---.
Column 8, line 25, in claim 18, subparagraph (d), "obervable" should be ---observable---.

Signed and Sealed this

Twenty-fourth Day of January, 1989

Attest:

DONALD J. QUIGG

Attesting Officer     Commissioner of Patents and Trademarks